United States Patent
Nanbu et al.

[11] Patent Number: 6,074,675
[45] Date of Patent: Jun. 13, 2000

[54] MINERAL COMPOSITION

[75] Inventors: Hironobu Nanbu; Katsuyasu Nakata; Noboru Sakaguchi; Yoshifumi Yamazaki, all of Yokkaichi, Japan

[73] Assignee: Taiyo Kagaku Co., Ltd., Mie, Japan

[21] Appl. No.: 09/077,600

[22] PCT Filed: Oct. 2, 1997

[86] PCT No.: PCT/JP97/03540

§ 371 Date: Jun. 2, 1998

§ 102(e) Date: Jun. 2, 1998

[87] PCT Pub. No.: WO98/14072

PCT Pub. Date: Apr. 9, 1998

[30] Foreign Application Priority Data

Oct. 3, 1996 [JP] Japan .................................. 8-283018
Feb. 21, 1997 [JP] Japan .................................. 9-054134

[51] Int. Cl.⁷ .................................................. A23L 1/304
[52] U.S. Cl. ............................ 426/74; 426/52; 426/662
[58] Field of Search ............................ 426/74, 52, 662

[56] References Cited

U.S. PATENT DOCUMENTS 4,849,132  7/1989  Fujita et al. ........................... 426/662
5,514,387  5/1996  Zimmerman et al. ................ 426/662
5,707,670  1/1998  Mehansho et al. ..................... 426/74
5,776,887  7/1998  Wilbert et al. ............................ 514/2

FOREIGN PATENT DOCUMENTS

63/173556  7/1988  Japan .

OTHER PUBLICATIONS

English Language Abstract of JP–A–9–238645.
English Language Abstract of JP–A–9–173028.
English Abstract of JP–A–56–117753 (Sep. 16, 1981).
English Abstract of JP–A–57–33540 (Feb. 23, 1982).
English Abstract of JP–A–57–110167 (Jul. 8, 1982).
English Abstract of JP–A–61–015645 (Jan. 23, 1986).
English Abstract of JP–A–63–173556 (Jul. 18, 1988).
English Abstract of JP–A–05–319817 (Dec. 3, 1993).
English Abstract of JP–A–63–276460 (Nov. 14, 1988).
English Abstract of JP–A–03–010659 (Jan. 18, 1991).
English Abstract of JP–A–05–049447 (Mar. 2, 1993).
English Abstract of JP–A–07–170953 (Jul. 11, 1995).

*Primary Examiner*—Helen Pratt
*Attorney, Agent, or Firm*—Birch, Stewart, Kolasch & Birch, LLP

[57] ABSTRACT

A mineral-containing composition including enzymatically decomposed lecithin and a water-insoluble mineral. Since the mineral composition shows excellent dispersion stability of the water-insoluble mineral, the mineral composition can be utilized in a wide variety of fields such as foods, cosmetics and industrial products.

12 Claims, 3 Drawing Sheets

MINERAL COMPOSITION

This application is the national phase under 35 U.S.C. §371 of prior PCT International Application No. PCT/JP97/03540 which has an International filing date of Oct. 2, 1997 now WO98/14072 which designated the United States of America, the entire contents of which are hereby incorporated by reference.

TECHNICAL FIELD

The present invention relates to a mineral composition, and food comprising the same. More particularly, the present invention relates to a mineral composition having excellent dispersibility, particularly excellent dispersibility in water phase, and food comprising the same.

BACKGROUND ART

In general, since the water-insoluble mineral has a high specific gravity of usually 1.5 or more, the water-insoluble mineral is easily precipitated in water. Therefore, in order to stably disperse the water-insoluble mineral in water, it is necessitated that the water-insoluble mineral is firstly made into fine particles.

As to methods for making the water-insoluble mineral into fine particles, there have been generally known physical crushing methods using a ball mill or jet mill. However, in this method, there is a limitation in obtaining fine particles having a particle size in the order of several microns, so that it is made impossible to stably disperse the fine particles in water.

As to methods for preparing fine particles having particle sizes in the order of submicrons, which are even smaller than those of the fine particles described above, there have been numerously reported chemical production methods utilizing reactions for forming salts by neutralization. According to this method, there can be produced ultrafine particles having a particle size of 1/100 microns. However, the resulting ultrafine particles are immediately formed into secondary agglomerates after its formation, so that there poses a problem in forming coarse particles having particle sizes in the order of microns.

In order to eliminate this problem, there have been proposed methods for adsorbing and retaining primary fine particles in the three-dimensional, network structure of crystalline cellulose or mucopolysaccharides by adding the crystalline cellulose and the mucopolysaccharides in water (Japanese Patent Laid-Open No. Sho 56-117753 and Japanese Examined Patent Publication No. Sho 57-35945); and methods of alleviating specific gravity by, when adding a water-insoluble mineral to fats and oils and dispersing the water-insoluble mineral therein, adjusting the content of the fats and oils in the resulting mixture so as to have the content to be 30% by weight or more (Japanese Patent Laid-Open No. Sho 57-110167). In any of these methods, however, since it is needed to contain large amounts of the substances other than the targeted water-insoluble mineral, there are defects in that the solute dispersed therein is diluted, and that the dispersibility of the water-insoluble mineral becomes drastically poor.

As to methods for eliminating the above defects, there have been developed a method for treating surfaces of fine particles of a water-insoluble mineral with an organic acid or an alkalizing agent (Japanese Patent Laid-Open No. Sho 61-15645); a method for adsorbing a surfactant, such as sucrose ester, to surfaces of fine particles of a water-insoluble mineral (Japanese Patent Laid-Open Nos. Sho 63-173556 and Hei 5-319817), and the like. In the former method, however, there is a defect in that the metal ions constituting the water-insoluble mineral are likely to be made into free ions in the water phase. In addition, in the latter method, there are defects in that the surfactant layer formed by adsorption to the surfaces of fine particles of a water-insoluble mineral is peeled off by heating for sterilization, and that secondary agglomeration of the fine particles takes place.

Incidentally, in general, there are many minerals as nutrients having low absorptivity when taken intracorporeally. Also, there are various defects in that those minerals having good absorptivity when taken intracorporeally have coloration, odors, or flavors, or those minerals may be easily reacted with other ingredients in food, and that irritability against mucous membranes of digestive tracts. For instance, as iron supplements, Japanese Patent Laid-Open Nos. Sho 63-276460, Hei 3-10659, Hei 5-49447, and Hei 7-170953 disclose iron porphyrin, ferritin, or lactoferrin, each of which is a natural-occurring iron material. However, since those iron materials have coloration and distinctive flavors, their applications to food are limited. In addition, since these nutrients are obtained by extraction from particular organs, there poses a problem in that mass production cannot be achieved owing to the necessity of complicated processes for its extraction.

Objects of the present invention are to provide a mineral composition having high thermal stability and excellent dispersibility without requiring large amounts of crystalline cellulose or fats and oils to be added to the water-soluble mineral, and food comprising the same.

Another objects of the present invention are to provide a mineral composition having high absorptivity when taken intracorporeally, substantially no coloration, odors, flavors, low reactivity with other ingredients in food, and small irritation against mucous membranes of digestive tracts, and food comprising the same.

These and other objects of the present invention will be apparent from the following description.

DISCLOSURE OF INVENTION

According to the present invention, there can be provided a mineral-containing composition comprising enzymatically decomposed lecithin and a water-insoluble mineral, and food comprising the mineral-containing composition mentioned above.

BEST MODE FOR CARRYING OUT THE INVENTION

The mineral composition of the present invention includes enzymatically decomposed lecithin and a water-insoluble mineral.

Because the mineral composition of the present invention includes the enzymatically decomposed lecithin, the composition has excellent dispersibility of the water-insoluble mineral.

As to the enzymatically decomposed lecithin, there can be favorably used at least one compound selected from the group consisting of monoacylglycerophospholipids containing, as main components, those obtained by treatment of limited hydrolysis of an ester moiety of a fatty acid of a plant lecithin or an egg yolk lecithin with phospholipase A, such as lysophosphatidylcholine, lysophosphatidylethanolamine, lysophosphatidylinositol and lysophosphatidylserine; and those obtained by treatment of limited hydrolysis of a fatty acid ester of a plant lecithin or an egg yolk lecithin with phospholipase D, such as phosphatidic acid, lysophosphatidic acid, phosphatidylglycerol and lysophosphatidylglycerol. Among them, lysophosphatidylcholine, lysophosphatidylethanolamine and lysophosphatidylserine are preferably used, and lysophosphatidylcholine is more preferably used. The phospholipases used in the enzymatic decomposition may be of any kind, as long as they have phospholipase A activity and/or phospholipase D activity, regardless of the origins such as animal-derived ones, such as porcine pancreas, plant-derived ones, such as cabbages, microorganism-derived ones, such as molds.

Any of those enzymatically decomposed lecithins have a surface activity, and its hydrophilic group moiety also similarly has a phosphate group, so that adsorption coating strength of surfaces of the water-insoluble mineral is remarkably strong as compared to nonionic surfactants such as sucrose esters of fatty acids and glycerol esters of fatty acids. Therefore, an adsorption interfacial layer of thermally stable, enzymatically decomposed lecithin is formed on the surfaces of fine particles of the water-insoluble mineral, and the adsorption interfacial layer is not peeled off when subjected to heat treatment, so that secondary agglomeration can be effectively inhibited. As a result, good dispersibility of the water-insoluble mineral can be obtained.

Incidentally, when using the enzymatically decomposed lecithin alone, sufficient dispersibility of the water-insoluble mineral can be obtained. However, when using the enzymatically decomposed lecithin together with other components, more superior dispersibility can be exhibited. Other components include metallic soaps, such as sodium oleate; alkyl ether surfactants, such as nonyl phenyl ether; polyoxyethylene adduct-type surfactants, such as Tween; nonionic surfactants; other surfactants, such as saponin compounds derived from quillaia and yuccha extract. Among them, the nonionic surfactant can be favorably used in the present invention because of increasing intracorporeal absorptivity of the mineral composition. It is desired that the nonionic surfactant is usually used so as to be contained in the mineral composition of the present invention in the range of from 0 to 20% by weight.

The nonionic surfactant is not particularly limited. It is desired that the nonionic surfactant has non-water-dissociating, hydroxyl group or an ether bond, as a hydrophilic group. The nonionic surfactants include, for example, polyglycerol esters of fatty acids, sucrose esters of fatty acids, glycerol esters of fatty acids, propylene glycol esters of fatty acids, sorbitan esters of fatty acids, pentaerythritol esters of fatty acids, sorbitol esters of fatty acids, and the like. Among them, the polyglycerol esters of fatty acids are preferably used. The polyglycerol esters of fatty acids of which constituent is a polyglycerol which contains 70% by weight or more of a polyglycerol having a degree of polymerization of 3 or more are more preferably used. The polyglycerol esters of fatty acids of which constituent is a polyglycerol which contains 70% by weight or more of a polyglycerol having a degree of polymerization of 3 to 11 are particularly preferably used.

The polyglycerol ester of a fatty acid is referred to an ester formed between a polyglycerol and a fatty acid, and its esterification ratio is not particularly limited. The kinds of the fatty acids are not particularly limited. In the present invention, it is desired that the fatty acid has hydroxyl group in a saturated or unsaturated, linear or branched fatty acid having 6 to 22 carbon atoms, preferably 8 to 18 carbon atoms, more preferably 12 to 14 carbon atoms.

Methods for preparing of the polyglycerol ester of a fatty acid are not particularly limited. The methods include a method comprising heating a fatty acid and a polyglycerol to a temperature of 200° C. or more, while removing water in the presence or absence of an acidic or alkali catalyst, thereby esterifying the product; a method comprising using an acid chloride or an acid anhydride corresponding to a fatty acid instead of the fatty acid, and reacting the acid chloride or the acid anhydride with a polyglycerol in a suitable organic solvent such as pyridine; a method comprising subjecting a polyglycerol to chemical treatment such as acetalization in advance, thereby esterifying the product; and after esterification, removing the resulting acetal, thereby inhibiting the formation of by-products; and a method comprising selectively esterifying a polyglycerol by using an enzyme in the non-water reactive system (an organic solvent system) containing minimally required amount of water. Of those methods, a method can be suitably selected.

Other components contained in the polyglycerol esters of fatty acids may be suitably separated and removed. The components can be removed by the methods including, for example, distillation methods, such as distillation under reduced pressure, molecular distillation, and steam distillation; extraction methods with suitable organic solvents; chromatography methods in which a column is packed with an adsorbent, a gel filtration agent, or the like. Also, among those methods, the extraction methods with the organic solvents and the chromatography methods can be favorably used from the practical viewpoint. According to the extraction methods with the organic solvents, target components can be easily obtained by adding water to a reaction mixture after reaction, extracting with an organic solvent, and then removing the organic solvent. The organic solvent may be those which are water-insoluble. The organic solvents include, for example, low molecular fats and oils, such as ethyl acetate, methyl acetate, petroleum ethers, hexane, diethyl ether, benzene, glycerol tricaprylate, and the like.

Compositions of the polyglycerol constituting the polyglycerol ester of a fatty acid are not particularly limited. In the present invention, the polyglycerol preferably contains 70% by weight or more of a polyglycerol having a degree of polymerization of 3 or more, and the polyglycerol more preferably contains 70% by weight or more of a polyglycerol having a degree of polymerization of 3 to 10. Also, the esterification ratio is not particularly limited. It is desired that the esterification ratio is 10 to 80%, preferably 10 to 60%, more preferably 10 to 30%.

Also, in the present invention, when used together with the enzymatically decomposed lecithin, a polyglycerol ester of a fatty acid of which constituent is a polyglycerol which contains 70% by weight or more of a polyglycerol having a degree of polymerization of 2 or more, preferably 3 to 10, more preferably 3 to 5, has extremely good dispersibility of the water-insoluble mineral. In this case, it is desired that the carbon atoms of the fatty acid which can be used as the constituent of the polyglycerol ester of a fatty acid are 6 to 22, preferably 8 to 18, more preferably 12 to 14.

As to the sucrose esters of fatty acids, there can be favorably used the sucrose esters of fatty acids of which constituents are saturated or unsaturated fatty acids having 12 to 22 carbon atoms, and the mean substitution degree is 1 to 2.5. Here, the mean substitution degree is referred to a mean bond number of a fatty acid esterified in one sucrose molecule.

The glycerol esters of fatty acids include esters formed between glycerol with a fatty acid, and mixtures of monoglycerides, diglycerides and triglycerides, which are obtained by transesterifications of glycerol with fats and oils. In the mixtures of monoglycerides, diglycerides and triglycerides, the content of the monoglycerides may be increased by subjecting the mixture to separation and purification treatments by the molecular distillations or the column methods, depending upon its use.

The propylene glycol esters of fatty acids comprise monoesters and diesters, each of which is obtained by esterification reaction of propylene glycol with a fatty acid, or transesterification reaction of propylene glycol with fats and oils.

The sorbitan esters of fatty acids are an ester formed between a fatty acid and sorbitan, which is a dehydrated product of sorbitol, a sweetening.

The glycerol esters of fatty acids, the propylene glycol esters of fatty acids and the sorbitan esters of fatty acids are not particularly limited, and those commercially available can be suitably selected.

Incidentally, the dispersibility of the water-insoluble mineral can be also improved by using mucopolysaccharides such as crystalline cellulose and xanthan gum; hydrophilic polymeric compounds such as polyvinyl alcohols, copolymers of vinyl acetate and polyvinyl alcohol, and the like. However, when no enzymatically decomposed lecithin is used, the dispersibility cannot be sufficiently improved by inhibiting secondary agglomeration of the water-insoluble minerals.

The water-insoluble minerals which can be used in the present invention are not particularly limited. The water-insoluble minerals include, for example, iron, calcium, magnesium, zinc, copper, and the like. Among them, iron, calcium and magnesium are favorably used, and iron is more favorably used.

The forms of the water-insoluble minerals generally include inorganic salts, organic salts, and the like.

The inorganic salts include, for example, iron salts, calcium salts, magnesium salts, zinc salts, copper salts, selenium salts, and the like. Each of those inorganic salts can be used alone or in admixture of two or more kinds.

The iron salts include, for example, iron chloride, iron hydroxide, ferric oxide, iron carbonate, iron lactate, ferric pyrophosphate, ferrous phosphate, iron sulfate, iron orotate, iron citrate, salts of iron citrate, iron gluconate, iron threonate, iron fumarate, and the like. Among them, ferric pyrophosphate, ferrous phosphate and salts of iron citrate can be favorably used in the present invention.

The calcium salts include, for example, calcium chloride, calcium citrate, calcium carbonate, calcium acetate, calcium oxide, calcium hydroxide, calcium lactate, calcium pyrophosphate, calcium phosphate, calcium sulfate, calcium gluconate, calcium glycerophosphate, echinus shell calcium, shell calcium, crab shell calcium, bovine bone calcium, fish bone calcium, coral calcium, milk serum calcium, egg shell calcium, and the like. Among them, calcium carbonate, calcium pyrophosphate, calcium phosphate, bovine bone calcium, shell calcium, milk serum calcium and egg shell calcium can be favorably used in the present invention.

The magnesium salts include, for example, magnesium acetate, magnesium oxide, magnesium hydroxide, magnesium carbonate, magnesium pyrophosphate, magnesium sulfate and the like. Among them, magnesium hydroxide and magnesium pyrophosphate can be favorably used in the present invention.

The zinc salts include, for example, zinc sulfate, zinc gluconate, and the like. Among them, zinc sulfate can be favorably used in the present invention.

The copper salts include, for example, copper ethylenediaminetetraacetate, copper acetate, copper sulfate, copper gluconate, and the like. Among them, copper gluconate can be favorably used in the present invention.

The selenium salts include, for example, sodium selenite, selenomethionine, selenocysteine, and the like. Among them, selenomethionine can be favorably used in the present invention.

The water-insoluble minerals which can be used in the present invention are not particularly limited. From the viewpoints of flavor, reactivity with food components, a irritability of mucous membrane of digestive tract, and the like, the water-soluble minerals having a solubility product in water at 25° C. of $1.0 \times 10^{-7}$ or less are used, and in particular, metal salts having a solubility product in water at 25° C. of $1.0 \times 10^{-7}$ or less are preferably used. The metal salts having a solubility product in water at 25° C. of $1.0 \times 10^{-7}$ or less can be used, for example, as colloids.

Concrete examples of the metal salts having a solubility product in water at 25° C. of $1.0 \times 10^{-7}$ or less include, for example, silver chloride (AgCl, a solubility product in water at 25° C.: $1.0 \times 10^{-10}$); silver pyrophosphate ($Ag_4P_2O_7$, a solubility product in water at 25° C.: $1.0 \times 10^{-21}$); aluminum hydroxide ($Al(OH)_3$, a solubility product in water at 25° C.: $2.0 \times 10^{-32}$); aluminum phosphate ($AlPO_4$, a solubility product in water at 25° C.: $5.8 \times 10^{-19}$); barium sulfate ($BaSO_4$, a solubility product in water at 25° C.: $1.0 \times 10^{-10}$); barium phosphate ($Ba_3(PO_4)_2$, a solubility product in water at 25° C.: $6.0 \times 10^{-39}$); barium carbonate ($BaCO_3$, a solubility product in water at 25° C.: $5.1 \times 10^{-9}$); calcium pyrophosphate ($Ca_2P_2O_7$, a solubility product in water at 25° C.: $2.0 \times 10^{-19}$); calcium phosphate ($Ca_3(PO_4)_2$, a solubility product in water at 25° C.: $2.0 \times 10^{-29}$); calcium carbonate ($CaCO_3$, a solubility product in water at 25° C.: $4.7 \times 10^{-9}$); ferrous hydroxide ($Fe(OH)_2$, a solubility product in water at 25° C.: $8.0 \times 10^{-16}$); ferrous phosphate ($Fe_3(PO_4)_2$, a solubility product in water at 25° C.: $1.3 \times 10^{-22}$); ferric pyrophosphate ($Fe_4(P_2O_7)_3$, a solubility product in water at 25° C.: $2.0 \times 10^{-13}$); ferrous carbonate ($FeCO_3$, a solubility product in water at 25° C.: $3.5 \times 10^{-11}$); magnesium hydroxide ($Mg(OH)_2$, a solubility product in water at 25° C.: $1.1 \times 10^{-11}$); magnesium pyrophosphate ($Mg_2P_2O_7$, a solubility product in water at 25° C.: $2.5 \times 10^{-13}$); cuprous chloride (CuCl, a solubility product in water at 25° C.: $3.2 \times 10^{-7}$); cupric carbonate ($CuCO_3$, a solubility product in water at 25° C.: $2.5 \times 10^{-10}$); manganese hydroxide ($Mn(OH)_2$, a solubility product in water at 25° C.: $1.6 \times 10^{-13}$); manganese sulfate ($MnSO_4$, a solubility product in water at 25° C.: $1.0 \times 10^{-11}$); nickel hydroxide ($Ni(OH)_2$, a solubility product in water at 25° C.: $2.7 \times 10^{-15}$); nickel phosphate ($Ni_3(PO_4)_2$, a solubility product in water at 25° C.: $4.5 \times 10^{-10}$); lead sulfate ($PbSO_4$, a solubility product in water at 25° C.: $1.7 \times 10^{-8}$); lead phosphate ($Pb_3(PO_4)_2$, a solubility product in water at 25° C.: $1.5 \times 10^{-13}$); zinc hydroxide ($Zn(OH)_2$, a solubility product in water at 25° C.: $7.0 \times 10^{-18}$); zinc pyrophosphate ($Zn_2P_2O_7$, a solubility product in water at 25° C.: $2.0 \times 10^{-8}$); and the like. Among the metal salts, phosphate salts, carbonate salts, iron salts and calcium salts, including, for example, calcium pyrophosphate ($Ca_2P_2O_7$, a solubility product in water at 25° C.: $2.0 \times 10^{-19}$); calcium phosphate ($Ca_3(PO_4)_2$, a solubility product in water at 25° C.: $2.0 \times 10^{-29}$); calcium carbonate ($CaCO_3$, a solubility product in water at 25° C.: $4.7 \times 10^{-9}$); ferrous phosphate ($Fe_3(PO_4)_2$, a solubility product in water at 25° C.: $1.3 \times 10^{-22}$); ferric pyrophosphate ($Fe_4(P_2O_7)_3$, a solubility product in water at 25° C.: $2.0 \times 10^{-13}$); magnesium hydroxide ($Mg(OH)_2$, a solubility product in water at 25° C.: $1.1 \times 10^{-11}$); magnesium pyrophosphate ($Mg_2P_2O_7$, a solubility product in water at 25° C.: $2.5 \times 10^{-13}$); cuprous chloride ($CuCl$, a solubility product in water at 25° C.: $3.2 \times 10^{-7}$); manganese sulfate ($MnSO_4$, a solubility product in water at 25° C.: $1.0 \times 10^{-11}$); and the like are preferably used. Ferrous phosphate, ferric pyrophosphate, calcium carbonate, pyrophosphate typically exemplified by calcium pyrophosphate, calcium phosphate, magnesium hydroxide and magnesium pyrophosphate are more preferably used. Ferric pyrophosphate and calcium carbonate are still more preferably used.

Here, the solubility product is a product of molar concentrations (mol/liter) of cations and anions in a saturated solution of salts. Among the solubility products and general solubilities, there is a correlation shown by the following equation.

Specifically, when the metal salt is denoted by $M_aX_b$, wherein a and b represents numbers of atoms of M and X, respectively, and the solubility is denoted by S, the solubility product (Ksp) is expressed by the equation:

$$Ksp = [M]^a[X]^b = (aS)^a(bS)^b = a^a \times b^b \times S^{(a+b)}$$

wherein inside the parentheses [ ] denotes ion densities expressed as mol/liter.

Taking calcium carbonate ($CaCO_3$) as one example, Ksp of $CaCO_3$ is $4.7 \times 10^{-9}$. When the values are plugged into the equation, the equation reads:

$$[Ca]^1[CO_3]^1 = S^2 = 4.7 \times 10^{-9}.$$

The solubility S of $CaCO_3$ is about $6.9 \times 10^{-5}$ mol/liter (6.9 ppm), so that it is found that $CaCO_3$ is water-insoluble.

From the above, the solubility of salts having a solubility product of more than $1.0 \times 10^{-7}$ is about $3.2 \times 10^{-3}$ mol/liter, which is about 100 times as large as the solubility of $CaCO_3$, so that the salts are not water-insoluble in a strict sense. By a slight change of pH in the water phase, free metal ions are formed from the salts on the surfaces of the water-insoluble mineral, which makes the solutions unstable, thereby inhibiting the formation of the adsorption interfacial layer of thermally stable enzymatically decomposed lecithin.

By contrast, in the present invention, since the water-insoluble mineral is used and secondary agglomeration of the water-insoluble mineral can be effectively inhibited, the shapes of primary fine particles of the water-insoluble mineral can be retained, so that stable dispersibility of the fine particles can be obtained.

The particle size of the water-insoluble mineral is not particularly limited. From the viewpoint of the dispersibility, it is desired that the particle size is 0.4 $\mu$m or less, and it is more desired that 80 vol % or more of the particles of the entire particles have a particle size of 0.2 $\mu$m or less. Methods for obtaining the water-insoluble mineral having the above particle size include, for example, physical crushing methods by means of, for example, homomixers, ball mills, jet mills, and the like; methods for forming salts by neutralization, and the like. Among the methods, from the viewpoint of easily obtaining fine particles with an even particle size, the methods for forming salts by neutralization is preferably used. Here, the methods for forming salts by neutralization are the methods for preparing salts by reacting acids and alkalis. The methods for forming salts by neutralization include, for example, a method for preparing a salt by a neutralization reaction of a strong acid with a strongly basic salt, including, for example, a method for preparing ferric pyrophosphate ($Fe_4(P_2O_7)_3$) by a neutralization reaction of ferric chloride ($FeCl_3$) with tetrasodium pyrophosphate ($Na_4P_2O_7$); a method of preparing a salt by a neutralization reaction of a weak acid with a strongly basic salt, including, for example, a method for preparing calcium carbonate ($CaCO_3$) by a neutralization reaction of carbonic acid ($H_2CO_3$) with calcium hydroxide ($Ca(OH)_2$). According to the methods for forming salts by neutralization, ultrafine particles with a particle size of 0.01 to 0.1 $\mu$m can be obtained.

In the mineral composition of the present invention, as occasion demands, in order to improve the dispersibility and stability of the mineral composition, there can be used additives including, for example, phospholipids such as lecithin; organic acid esters of monoglycerides, such as monoglyceride citrate, succinylated monoglyceride, acetylated monoglyceride, diacetyl tartaric acid esters of monoglyceride and lactated monoglyceride. Incidentally, the lecithin is a general trade name, which is a generic term for the phospholipids.

Methods for preparation of the mineral composition of the present invention are not particularly limited. The methods include, for example, a method comprising dissolving the enzymatically decomposed lecithin in an aqueous solution of a metal salt used as a water-insoluble mineral; a method comprising dispersing a metal salt, as a water-insoluble mineral, in an aqueous solution of the enzymatically decomposed lecithin, and the like.

As mentioned above, the mineral composition of the present invention includes the enzymatically decomposed lecithin and the water-insoluble mineral.

The mineral composition of the present invention can be used in powdery state, and it can be used also in water-dispersed state containing water.

In this case, from the viewpoint of the dispersibility of the water-insoluble mineral, it is desired that the content of the enzymatically decomposed lecithin in the mineral composition of the present invention is 0.01% by weight or more, preferably 0.1% by weight or more. Also, in order not to give poor influence in the flavor of food when using the enzymatically decomposed lecithin in foods, it is desired that the content of the enzymatically decomposed lecithin in the mineral composition is 20% by weight or less, preferably 15% by weight or less.

From the economic viewpoint, it is desired that the content of the water-insoluble mineral in the mineral composition is 1% by weight or more, preferably 10% by weight or more. Also, from the viewpoints of the fluidity and operating ability upon addition of the water-insoluble mineral, it is desired that the content of the water-insoluble mineral in the mineral composition is 50% by weight or less, preferably 30% by weight or less.

From the viewpoints of the maintaining dispersion stability of the mineral composition and operating ability, it is desired that the content of water in the mineral composition is 40% by weight or more, preferably 65% by weight or more. Also, from the economic viewpoint, it is desired that the content of water in the mineral composition is 80% by weight or less, preferably 75% by weight or less.

When the other constituents are contained in the mineral composition of the present invention, the content of the other constituents in the mineral composition may be suitably adjusted within the range so as not to impair the purpose of the present invention. Use of the mineral composition of the present invention is not particularly limited. The use includes, for example, food, drugs, feeds, cosmetics, industrial products, and the like.

The foods containing the mineral composition of the present invention include, for example, wheat flour processed foods typically exemplified by bread, noodles, and the like; rice processed goods such as rice gruel and rice cooked with meat and vegetables; sweets such as crackers, cakes, candies, chocolates, rice crackers, rice-cake cubes, tablet sweets and Japanese sweets; soybean processed foods such as tofu and processed foods thereof; drinks such as soft drinks, fruit juice drinks, milk-based beverages, lactic acid bacilli drinks, soda pops and alcoholic beverages; dairy products such as yogurt, cheese, butter, ice cream, coffee whitener, whipped cream and milk; seasonings such as soy source, soybean paste, salad dressing, sauce, soup, margarine and mayonnaise; processed meet products for foods, such as ham, bacon and sausage; processed marine products such as kamaboko fish paste, hampen fish cake, chikuwa fish paste and canned fish meat; oral and enteral nourishing meals such as concentrated liquid food, half-digested conditional nourishing meal and nutrient nourishing meal. Incidentally, by adding the mineral composition of the present invention containing the water-insoluble mineral, typically exemplified by water-insoluble salts such as calcium carbonate and ferric pyrophosphate composition, to the food, those which are apt to be deficient in the body, such as calcium and iron, can be supplemented and enriched. Particularly, in liquid foods typically exemplified by beverages, as to addition of the water-insoluble salts, the water-insoluble mineral sediments quickly, so that the applications range of the water-insoluble salts has conventionally been quite narrow. On the other hand, when using the mineral composition of the present invention, the minerals can be enriched while keeping good flavor of the liquid food and a stable state of the liquid food. For example, in the field of foods, a calcium- or iron-enriched beverage, such as milk, a lactic acid beverage, a soft drink or a soda pop, which has dispersion stability can be produced by preparing a calcium carbonate composition or ferric pyrophosphate composition, and then adding it to the beverage. The amount of the mineral composition of the present invention added to food is not particularly limited, and it may be suitably determined depending upon the kinds of metal salts, the forms of food and feeds which are added, and sex and age of human and domestic animals.

The feeds containing the mineral composition of the present invention include, for example, feeds for pets, domestic animals, cultured fishes, and the like.

The cosmetics containing the mineral composition in the present invention include lotion; milky lotion; bathing agents; detergents such as cleansing agents; dentifrices, and the like. Among them, particularly in the bathing agent, damages on bathtubs can be inhibited by precipitating salts such as calcium carbonate which are used as a main ingredient.

The industrial products containing the mineral composition in the present invention include films for agricultural purposes, sheet materials for walls or floors, fire-proofing agents to be added to resins, and the like. For this purpose, water-insoluble minerals such as calcium carbonate, barium sulfate, magnesium hydroxide and zinc hydroxide are used. The water-insoluble mineral disperses stably in the resinous base materials, so that the functional properties such as physical strength after molding, slidability of the surface and fire-proofing properties, can be improved.

The present invention will be concretely explained hereinbelow based on Examples.

EXAMPLE 1

In 60 kg of ion-exchanged water were dissolved 13 kg of ferric chloride hexahydrate and 0.3 kg of enzymatically decomposed lecithin (trade name: "SUNLECITHIN L," manufactured by Taiyo Kagaku Co., Ltd.) to prepare an iron solution.

To a pyrophosphate solution prepared by dissolving 20 kg of tetrasodium pyrophosphate decahydrate in 500 kg of ion-exchanged water was gradually added the iron solution prepared above with stirring. The pH of the resulting mixture was then adjusted to 3.0. After forming of the salt of ferric pyrophosphate by neutralization reaction was terminated, the resulting reaction mixture was subjected to solid-liquid separation by centrifugation (3000×g, for 5 minutes). Thereafter, 8.2 kg of a ferric pyrophosphate-enzymatically decomposed lecithin complex, calculated as weight of dry basis, formed in the solid phase was collected, and the resulting complex was then re-suspended in ion-exchanged water, to give a 10%-ferric pyrophosphate slurry, Product I.

Comparative Example 1

In 60 kg of ion-exchanged water was dissolved 13 kg of ferric chloride hexahydrate to prepare an iron solution.

To a pyrophosphate solution prepared by dissolving 20 kg of tetrasodium pyrophosphate decahydrate in 500 kg of ion-exchanged water was gradually added the iron solution prepared above with stirring. The pH of the resulting mixture was then adjusted to 3.0.

Next, the resulting reaction mixture was subjected to solid-liquid separation in the same manner as in Example 1. Thereafter, 8 kg of ferric pyrophosphate, calculated as weight of dry basis, formed in the solid phase was collected, and the resulting product was then re-suspended in ion-exchanged water, to give a 10%-ferric pyrophosphate slurry, Reference Product A.

Comparative Example 2

The same procedures as in Example 1 were carried out except that the enzymatically decomposed lecithin in Example 1 was replaced with a sucrose ester of a fatty acid (trade name: "RYOTO SUGAR ESTER S-1570," manufactured by Mitsubishi Chemical Corporation), to give a 10%-ferric pyrophosphate slurry, Reference Product B.

As the properties of Product I and Reference Products A and B prepared in Example 1 and Comparative Examples 1 and 2, the water dispersibility and the particle size distribution were evaluated according to the following methods.

[Water Dispersibility]

To 100 g of each of Product I and Reference Products A and B prepared in Example 1 and Comparative Examples 1 and 2, each being a 10%-ferric pyrophosphate slurry, was added 900 g of commercially available milk. The precipitating property when the concentration of ferric pyrophosphate is 1% was evaluated with the passage of time.

As a result, in Reference Product A, almost 100% of the resulting product precipitated after allowing it to stand for 10 minutes, and in Reference Product B, about 90% of the resulting product precipitated after allowing it to stand for 6 hours.

By contrast, in Product I prepared in Example 1, no precipitation formed even after the passage of time of 500 hours.

Particle Size Distribution

Figure 1A:
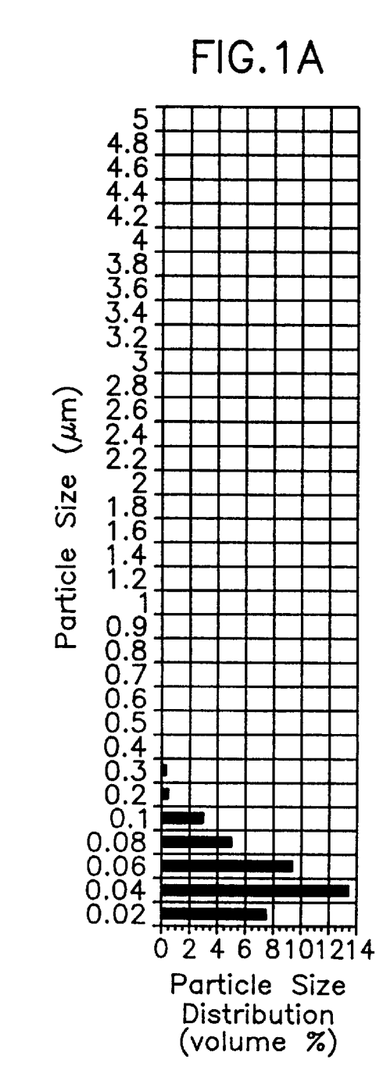
FIG. 1 is graphs showing particle size distributions of Product I obtained in Example 1, Reference Product A obtained in Comparative Example 1, and Reference Product B obtained in Comparative Example 2.
Figure 1B:
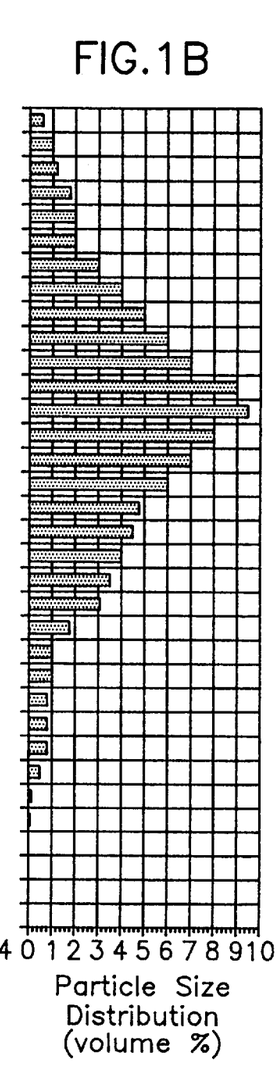
Figure 1C:
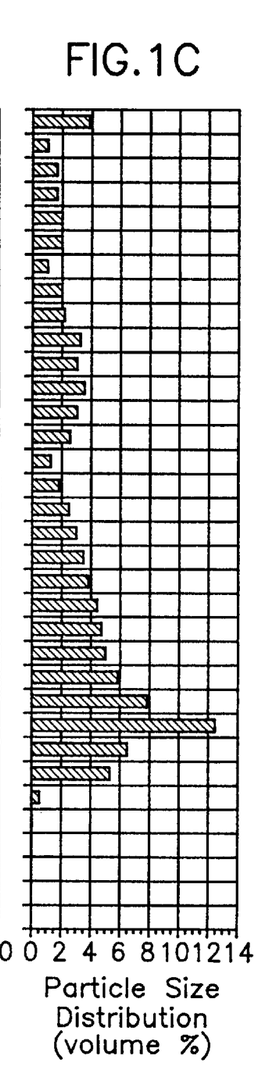

Each of the particle size distributions of Product I and Reference Products A and B, each being a 10%-ferric pyrophosphate slurry, was measured by using a laser diffraction particle size distribution analyser (trade name "HELOS," manufactured by SYMPATEC). The results are shown in FIG. 1. In FIG. 1, (A), (B), and (C) are graphs showing particle size distributions of Product I, Reference Product A, and Reference Product B, respectively.

It is clear from the results of the particle size distributions shown in FIG. 1 and the water dispersibility that since Product I prepared in Example 1 (particle size distribution: 0.01 to 0.3 µm) has an extremely small particle size, as compared to Reference Product A prepared in Comparative Example 1 (particle size distribution: 0.2 to 5 µm) and Reference Product B prepared in Comparative Example 2 (particle size distribution: 0.2 to 3 µm), Product I is uniformly dispersed in water.

It is clear from the above that iron-fortified milk having stable iron dispersibility can be obtained according to Example 1.

EXAMPLE 2

In 120 kg of ion-exchanged water were dissolved 20 kg of calcium chloride dihydrate and 3 kg of enzymatically decomposed lecithin (trade name: "SUNLECITHIN L," manufactured by Taiyo Kagaku Co., Ltd.) to prepare a calcium solution.

To a solution prepared by dissolving 11 kg of sodium carbonate and 14 kg of a polyglycerol ester of a fatty acid (trade name: "SUNSOFT A-12E," manufactured by Taiyo Kagaku Co., Ltd.) in 260 kg of ion-exchanged water was gradually added the calcium solution prepared above with stirring. The pH of the resulting mixture was then adjusted to 9.0.

After forming of the salt of calcium carbonate by neutralization reaction was terminated, the resulting reaction mixture was subjected to solid-liquid separation by centrifugation (3000×g, for 5 minutes). Thereafter, 10 kg of calcium carbonate, calculated as weight of dry basis, formed in the solid phase was collected, and the resulting product was then re-suspended in ion-exchanged water, to give a 10%-calcium carbonate slurry, Product II.

Comparative Example 3

In 120 kg of ion-exchanged water was dissolved 20 kg of calcium chloride dihydrate to prepare a calcium solution.

To a solution prepared by dissolving 11 kg of sodium carbonate in 260 kg of ion-exchanged water was gradually added the calcium solution prepared above with stirring. The pH of the resulting mixture was then adjusted to 9.0.

After forming of the salt of calcium carbonate by neutralization reaction was terminated, the resulting reaction mixture was subjected to solid-liquid separation by centrifugation (3000×g, for 5 minutes). Thereafter, 8 kg of calcium carbonate, calculated as weight of dry basis, formed in the solid phase was collected, and the resulting product was then re-suspended in ion-exchanged water, to give a 10%-calcium carbonate slurry, Reference Product C.

Next, the transparency of Product II prepared in Example 2 and Reference Product C prepared in Comparative Example 3, each being a 10%-calcium carbonate slurry, was evaluated according to the following method.

Transparency

In 200 parts by weight of a 10%-aqueous solution of a polyvinyl alcohol (manufactured by Wako Pure Chemical Industries) was dispersed 200 parts by weight of each of Product II prepared in Example 2 or Reference Product C prepared in Comparative Example 3, each being a 10%-calcium carbonate slurry. Thereafter, the resulting mixture was applied to a surface of glass in a thickness of 1 mm, and the coated glass was dried in an oven at 120° C. The transparency of the resulting coating film was observed by gross examination.

As a result, in contrast to Product II prepared in Example 2 had a good transparency, Reference Product C prepared in Comparative Example 3 showed spotted agglomeration of $CaCO_3$, and the resulting coating film did not have sufficient transparency.

EXAMPLE 3

In 100 liters of warm water at 40° C. were dissolved 10 g of sodium carbonate, 7 g of sodium hydrogencarbonate, and 0.02 g of Food Yellow No. 4 (manufactured by Saneigen F. F. I. Co., Ltd., compound name: Tartrazine), to prepare a bathing agent solution.

To the resulting bathing agent solution was added 50 ml of Product II prepared in Example 2 or Reference Product C prepared in Comparative Example 3, each being a 10%-calcium carbonate slurry. The state of precipitation of calcium carbonate when kept standing was observed.

As a result, in the case where Reference Product C prepared in Comparative Example 3 was used, the comparative test, entire calcium carbonate precipitated in about 20 minutes.

By contrast, in the case where Product II prepared in Example 2 was used, Example 3, no precipitation was formed even after passage of time of 100 hours or more.

EXAMPLE 4

In 883 kg of ion-exchanged water were dissolved 90 g of ferric pyrophosphate, 27 g of pentaglycerol monomyristate having a content of polyglycerol having a degree of polymerization of 3 to 11: 94% by weight, and 8 g of the enzymatically decomposed lecithin. The resulting mixture was sufficiently stirred and dispersed using a homomixer, to give 1.0 kg of a 10%-suspension of a ferric pyrophosphate composition, Product III.

EXAMPLE 5

In 883 g of ion-exchanged water were dissolved 90 g of ferric pyrophosphate, 22.5 g of pentaglycerol monomyristate having a content of polyglycerol having a degree of polymerization of 3 to 11: 94% by weight, and 4.5 g of the enzymatically decomposed lecithin. The resulting mixture was sufficiently stirred and dispersed using a homomixer, to give 1.0 kg of a 10%-suspension of a ferric pyrophosphate composition, Product IV.

EXAMPLE 6

In 6 kg of ion-exchanged water were dissolved 1.3 kg of ferric chloride hexahydrate and 30 g of the enzymatically decomposed lecithin to prepare an iron solution.

To a pyrophosphate solution prepared by dissolving 2 kg of tetrasodium pyrophosphate decahydrate and 170 g of pentaglycerol monomyristate having a content of polyglycerol having a degree of polymerization of 3 to 11: 94% by weight in 50 kg of ion-exchanged water was gradually added the iron solution prepared above with stirring. The pH of the resulting mixture was then adjusted to 3.0.

After forming of the salt of ferric pyrophosphate by neutralization reaction was terminated, the resulting reaction mixture was subjected to solid-liquid separation by centrifugation (3000×g, for 5 minutes). Thereafter, 860 g of a ferric pyrophosphate composition, calculated as weight of dry basis, in the solid phase was collected, and a part of the resulting composition was then re-suspended in ion-exchanged water, to give 4300 g of a 10%-suspension of a ferric pyrophosphate composition, Product V.

The particle size distribution of ferric pyrophosphate contained in the resulting Product V was evaluated in the same manner as in Example 1. As a result, the distribution was found to be from 0.01 to 0.3 μm.

Further, the remaining Product V was diluted with water, to prepare a 20%-ferric pyrophosphate composition solution. Thereafter, the resulting solution was dried by spray-drying method, to give 410 g of ferric pyrophosphate composition powder, Product VI.

Comparative Example 4

In 6 kg of ion-exchanged water was dissolved 1.3 kg of ferric chloride hexahydrate to prepare an iron solution.

To a pyrophosphate solution prepared by dissolving 2 kg of tetrasodium pyrophosphate decahydrate in 50 kg of ion-exchanged water was gradually added the iron solution prepared above with stirring. The pH of the resulting mixture was then adjusted to 3.0.

Next, the resulting reaction mixture was subjected to solid-liquid separation in the same manner as in Example 4. Thereafter, 0.78 kg of ferric pyrophosphate, calculated as weight of dry basis, in the solid phase was collected. The resulting product was then re-suspended in ion-exchanged water, to give 7.7 kg of a 10%-ferric pyrophosphate slurry, Reference Product D.

The particle size distribution of ferric pyrophosphate contained in the resulting Reference Product D was evaluated in the same manner as in Example 1. As a result, the distribution was found to be from 0.2 to 5 μm.

Comparative Example 5

To 2.0 kg of Reference Product D, a 10%-ferric pyrophosphate slurry, prepared in Comparative Example 4 was added 30 g of the enzymatically decomposed lecithin. The resulting mixture was sufficiently stirred, to prepare 2.02 kg of a 10%-ferric pyrophosphate slurry containing the enzymatically decomposed lecithin, Reference Product E.

Test Example 1
Assaying of Iron in Sera by Administration of Various Chalybeate1

A group of ten SD-male rats of 10 week old was fasted for 18 hours. Thereafter, each of Products III to V prepared in Examples 4 to 6 and Reference Products D and E prepared in Comparative Examples 4 and 5 was dissolved in distilled water. The resulting solution made into concentrations of 2 mg iron/kg equivalency for one rat was forcibly orally administered to a rat with a conductor.

Figure 2:
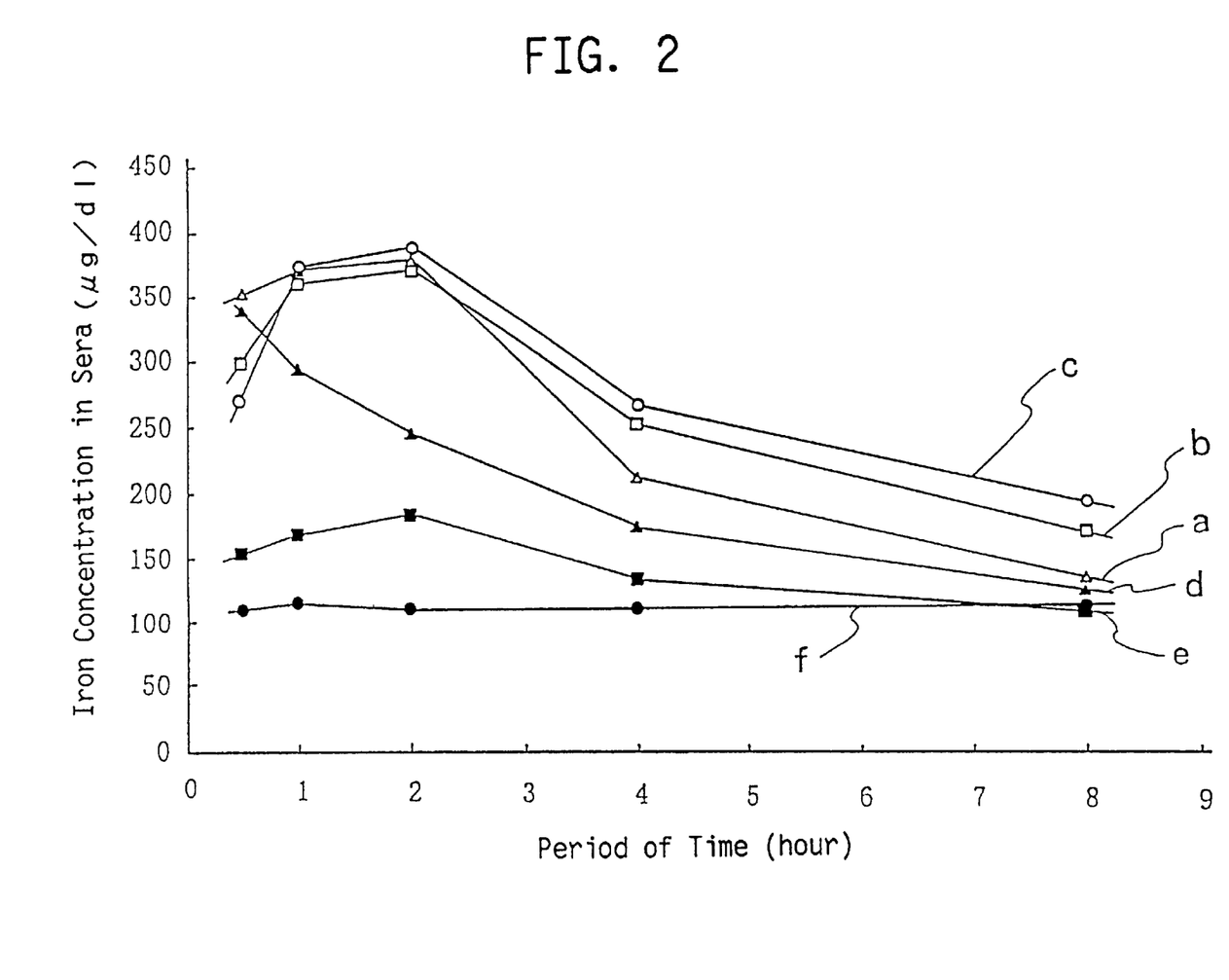
FIG. 2 is a graph showing the iron concentration in sera with respect to the passage of time after administering each of chalybeate prepared by using suspensions of each of ferric pyrophosphate compositions obtained in Examples 4 to 6 and Comparative Examples 4 and 5.

Also, only water, used as a blank solution, was orally administered in the same manner as above. After administration, blood was drawn from jugular after the passage of time of 0.5 hours, one hour, two hours, four hours, or eight hours, and sera were immediately separated from each of drawn blood samples. Thereafter, the iron (iron in sera) concentration in sera was measured according to a standard method of International Committee for Standardization in Hematology. The results thereof are shown in FIG. 2. In FIG. 2, a, b, c, d, e, and f denote data for Product III, Product IV, Product V, Reference Product D, Reference Product E, and water, respectively.

It is clear from the results shown in FIG. 2 that in Reference Products D and E prepared in Comparative Examples 4 and 5, the iron concentrations in sera in the passage of time show the maximal iron concentration in sera in a period of 30 minutes to one hour after administration, and thereafter the iron concentrations are drastically lowered.

By contrast, in Products III to V prepared in Examples 4 to 6, the iron concentrations in sera show the maximal iron concentration in sera after two hours, and thereafter the iron concentrations in sera are gradually lowered.

Next, the areal portions underneath the curve showing a total amount of iron in sera after 0.5 hours to eight hours from chalybeate administration are shown in Table 1.

TABLE 1

| Item | Maximal Concentration in Blood (μg/dl) | Iron Concentration in Sera after 8 hours from Administration (μg/dl) | Areal Portion Underneath Curve for Iron Concentration in Sera after 0.5 to 8 hours from Administration [(μg/dl) · Hour] |
|---|---|---|---|
| Product III | 380 (2) | 137 | 1853 |
| Product IV | 371 (2) | 171 | 2003 |
| Product V | 389 (2) | 194 | 2114 |
| Reference Product D | 340 (0.5) | 128 | 1460 |
| Reference Product E | 185 (1) | 110 | 1069 |
| Water | 117 | 113 | 853 |

(Remark)
( ): Inside parentheses show a period of time needed to reach the maximal concentration in blood.

It is clear from the results shown in Table 1 that the areal portions underneath the curve of the iron in sera of Products III to V have significantly high values with a level of significance of 5% as compared to Reference Products D and E.

In other words, since the level of the iron concentration in sera rises by the chalybeate administration, Products III and V have clearly higher iron absorptivity and milder decrease in the iron concentration in sera as compared to Reference Products D and E, so that high iron concentrations in sera are maintained even after eight hours. From the above, it is found that an excellent sustained-release property is exhibited.

Test Example 2
Test for Tolerance Dose of Stomach by Repetitious Administration

A group of eleven SD-male rats of 10 week old was fasted for 48 hours. Thereafter, each of Product IV prepared in Example 5, Reference Product D prepared in Comparative Example 4, and commercially available ferrous sulfate was dissolved in distilled water. Each of the resulting solutions made into concentrations of 30 mg iron/kg equivalency for one rat was forcibly orally administered to a rat with a probe thrice within 24 hours.

After five hours from the final administration, the stomach was enucleated, and the tolerance dose of stomach showing the extent of formation of gastric ulcer was evaluated by Adami method. The evaluation results thereof are shown in Table 2.

Incidentally, the numerical figures of evaluation in Table 2 mean the following:

0: No formation of ulcer.
1: Presence of hemorrhagic bands.
2: One to five small ulcers, each having 3 mm or less diameter.
3: One to five small ulcers, or one large ulcer.
4: Several large ulcers.
5: Some ulcers with open holes.

TABLE 2

| Rat No. | Product IV | Reference Product D | Ferrous Sulfate |
| --- | --- | --- | --- |
| 1 | 0 | 0 | 1 |
| 2 | 0 | 0 | 1 |
| 3 | 0 | 1 | 2 |
| 4 | 0 | 0 | 2 |
| 5 | 0 | 0 | 1 |
| 6 | 0 | 1 | 1 |
| 7 | 0 | 0 | 0 |
| 8 | 0 | 1 | 1 |
| 9 | 0 | 2 | 1 |
| 10 | 0 | 1 | 1 |
| 11 | 0 | 0 | 1 |
| Mean | 0 | 0.5 | 1.2 |
| Standard Deviation | 0 | 0.5 | 0.6 |

It is clear from the results shown in Table 2 that the formation of gastric ulcer could be partially observed in Reference Product D, whereas no changes in lesion were found in Product IV.

In other words, it is found that Product IV shows smaller influence against the digestive tract than that of Reference Product D.

Test Example 3

Figure 3A:
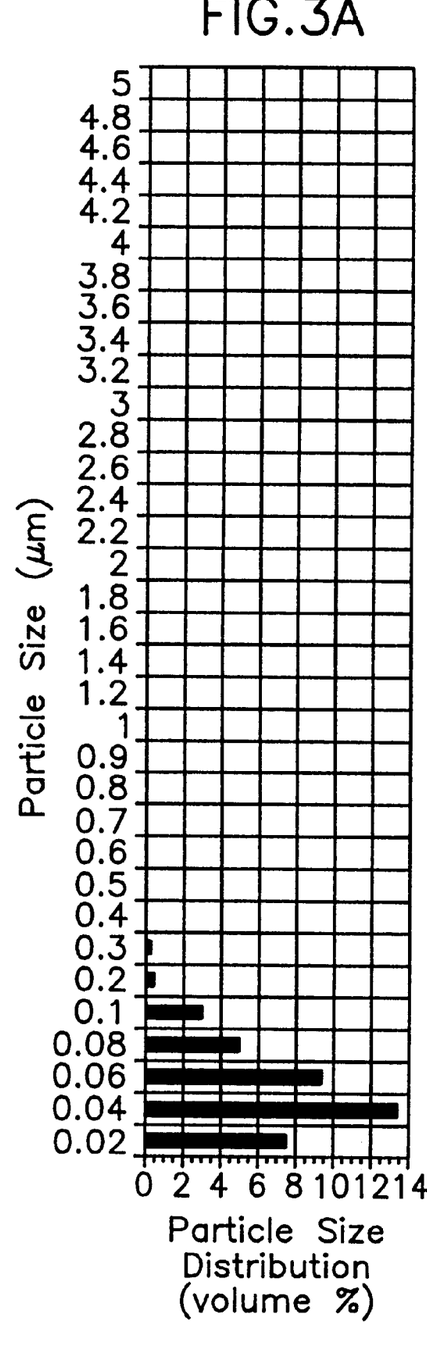
FIG. 3 is graphs showing particle size distributions of Product V obtained in Example 6, and Reference Product D obtained in Comparative Example 4.
Figure 3B:
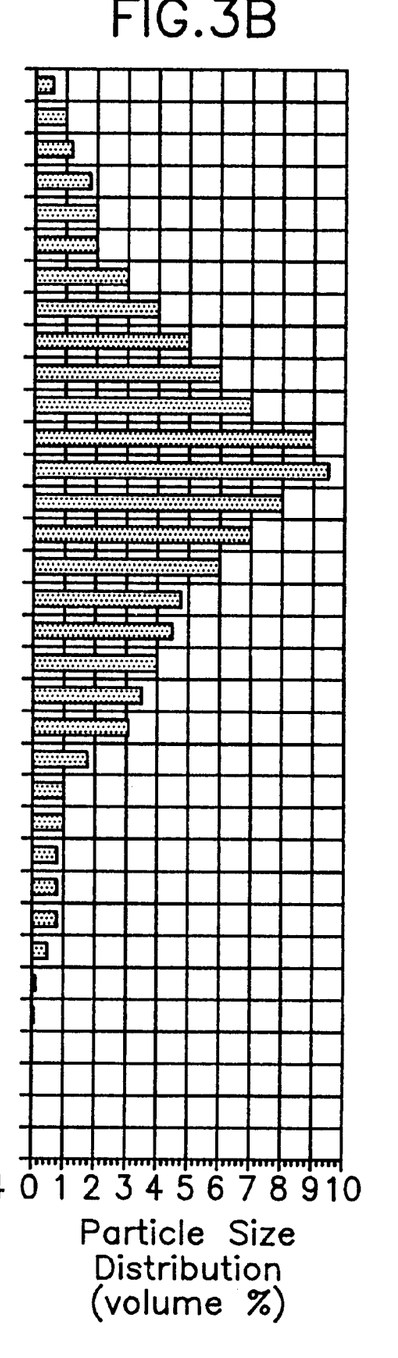

For each of the testing solutions prepared by diluting Product V prepared in Example 6 or Reference Product D prepared in Comparative Example 4 with water 50 times, the particle size distribution was evaluated by laser diffraction particle size distribution analyser (trade name: "HELOS," manufactured by SYMPATEC). The results thereof are shown in FIG. 3. In FIG. 3, (A) and (B) are graphs showing the particle size distributions of Product V and Reference Product D, respectively.

It is clear from the results shown in FIG. 3 and the results shown in Table 2 that Product V (particle size distribution: 0.01 to 0.3 $\mu$m) prepared in Example 6 had far smaller particles as compared to Reference Product D (particle size distribution: 0.2 to 5 $\mu$m) prepared in Comparative Example 4. Therefore, it presumably shows high intracorporeal absorptivity.

Test Example 4

To 100 ml of commercially available milk was respectively added Product III prepared in Example 4 and commercially available iron porphyrin to allow dissolution so as to have each iron content of 2 mg. Thereafter, sensory tests for strange flavor and odor were conducted by ten panelists. The evaluation results thereof are shown in Table 3.

TABLE 3

| | Strange Flavor (Number of Persons) | | | Odor (Number of Persons) | | |
| --- | --- | --- | --- | --- | --- | --- |
| Item | Strong | Weak | Little | Strong | Weak | Little |
| Product III | 0 | 2 | 8 | 0 | 1 | 9 |
| Iron Porphyrin | 3 | 6 | 1 | 4 | 4 | 2 |

It is clear from the results shown in Table 3 that Product III is so excellent that it has little strange flavors and odors as compared to the iron porphyrin.

Incidentally, in the case where the iron porphyrin was added to milk, the resulting mixture indicated black coloration, so that all of the panelists hesitated to drink it.

Preparation Example 1

In 6.7 kg of water were dispersed 3 kg of egg shell calcium, 100 g of pentaglycerol monocaprate having a degree of polymerization of 3 or more: 97%; and a degree of polymerization of 3 to 11: 94%), and 200 g of the enzymatically decomposed lecithin. Thereafter, the resulting mixture was passed through an ultrahigh-pressure homogenizer, to give a 30% egg shell calcium composition.

Preparation Example 2

In 120 kg of ion-exchanged water were dissolved 20 kg of calcium chloride dehydrate and 3 kg of the enzymatically decomposed lecithin to prepare a calcium solution.

To a solution prepared by dissolving 11 kg of sodium carbonate and 14 kg of pentaglycerol monocaprate having a content of a polyglycerol having a degree of polymerization of 3 to 11: 94% by weight in 260 kg of ion-exchanged water was gradually added the calcium solution prepared above with stirring. The pH of the resulting mixture was adjusted to 9.0.

After the reaction for forming the salt of calcium carbonate by neutralization reaction was terminated, the resulting reaction mixture was subjected to solid-liquid separation by centrifugation (3000×g, for 5 minutes). Thereafter, 10 kg of calcium carbonate, calculated as weight of dry basis, formed in the solid phase was collected, and the resulting product was re-suspended in ion-exchanged water, to give a 10% calcium carbonate composition.

Preparation Example 3

To 750 ml of water were added 100 g of fructose-glucose-liquid sugar, 2.0 g of citric acid, 0.5 g of sodium citrate, 2.0 g of Product III prepared in Example 4, and suitable amounts of perfume and colorants. After mixing the resulting mixture, water was added thereto to make up a total volume of 1000 ml, to give an ironfortified soft drink.

Next, the resulting iron-fortified soft drink was packed in a bottle with a 100 ml portion each. Thereafter, the soft-drink filled bottle was sterilized with heating for 10 minutes after reaching 90° C., to prepare an iron-fortified soft drink containing iron 6 mg/100 ml.

Preparation Example 4

Water was added to 51 g of sodium caseinate, 13.5 g of coleseed oil, 13.5 g of MCT, 122 g of dextrin, 20 g of white sugar, 1.0 g of succinylated monoglyceride, 1.0 g of the enzymatically decomposed lecithin, 2.0 g of milk flavoring, 1.8 g of potassium chloride, 10.5 mg of vitamin A powder, 1.3 mg of hydrochloride of vitamin $B_1$, 0.8 mg of vitamin $B_2$, 4.0 mg of hydrochloride of vitamin $B_6$, 84 mg of vitamin C, 0.6 mg of vitamin D powder, 158 mg of vitamin E powder, 25 mg of nicotinic acid amide, 10.5 mg of calcium pantothenate, 4.2 mg of folic acid, 1.0 g of Product III prepared in Example 4, and 3.0 g of the 10%-calcium carbonate composition solution prepared in Preparation Example 2 to make up a volume of one liter. The resulting mixture was mixed in a mixer, and then emulsified using a high-pressure homogenizer at a pressure of 200 kg/cm². Subsequently, the resulting emulsion was packed into an aluminum pouch in an amount of 200 ml each. The pouch was sealed, and subjected to retorting, to give a liquid enteral formula containing iron 3 mg/100 ml, and calcium 120 mg/100 ml.

Preparation Example 5

The amount 1.0 kg of Product VI prepared in Example 6, 2.5 kg of glucose, 2.0 kg of lactose, 2.4 kg of cornstarch, 2.0 kg of avicel, and 0.1 kg of magnesium stearate were mixed. Thereafter, the resulting mixture was granulated and formed into tablets using a tableting machine, to prepare round-shaped iron supplement tablet sweets containing iron 30 mg/g and having a diameter of 10 mm.

Preparation Example 6

The amount 200 g of margarine was kneaded together with a whip until its texture was smoothened. The amount 230 g of sugar was then gradually added to the resulting mixture, and the mixture was further kneaded. Thereafter, 73 g of a whole egg, 34 g of milk, 4.0 g of Product IV prepared in Example 5, and 3.0 g of vanilla essence were sequentially added thereto, and the entire content was sufficiently mixed. Next, 440 g of wheat flour was added to the resulting mixture, while passing through a sieve. The mixture was softly mixed to prepare a dough. Formed products of a given shape were prepared from the dough, and the resulting formed products were arranged on a cookie sheet. The formed products were baked at 170° C., to give iron-fortified cookies containing iron 12 mg/100 g.

Preparation Example 7

To 800 g of pork were added 2.0 g of Product III prepared in Example 4, 20 g of table salt, 3.0 g of sodium pyrophosphate, 6.0 g of sodium ascorbate and 10 g of sucrose. The flavored pork was preserved in salt at 10° C. for 72 hours, and then seasonings and spices were added thereto to give minced pork. The resulting minced pork was stuffed into a casing, and an iron-fortified sausage containing iron 7.1 mg/100 g was then prepared according to a conventional method.

INDUSTRIAL APPLICABILITY

Since the mineral composition of the present invention shows excellent dispersion stability of the water-insoluble mineral, the mineral composition can be utilized in a wide variety of fields such as foods, cosmetics and industrial products.

In addition, when containing a nonionic surfactant, since the mineral composition of the present invention has high absorptivity from the digestive tract and excellent sustained-release properties, the use of only a small amount gives sufficient effects. Further, since side-effects are less likely to take place, the mineral composition can be applied in a wide range of fields such as foods, feeds and drugs.

What is claimed is:

1. A mineral-containing composition comprising enzymatically decomposed lecithin and a water-insoluble mineral wherein said water-insoluble mineral comprises fine particles having a particle size of 0.4 µm or less.

2. The mineral-containing composition according to claim 1, wherein said enzymatically decomposed lecithin is at least one compound selected from the group consisting of lysophosphatidylcholine, lysophosphatidylethanolamine, lysophosphatidylinositol and lysophosphatidylserine, each being obtainable by treatment with phospholipase A; and phosphatidic acid, lysophosphatidic acid, phosphatidylglycerol and lysophosphatidylglycerol, each being obtainable by treatment with phospholipase D.

3. The mineral-containing composition according to claim 1, wherein said water-insoluble mineral is a colloid of a metal salt having a solubility product in water at 25° C. of 1.0 to $10^{-7}$ or less.

4. The mineral-containing composition according to claim 1, wherein said water-insoluble mineral is ferric pyrophosphate, calcium carbonate, calcium phosphate or calcium pyrophosphate.

5. The mineral-containing composition according to claim 1, further comprising a nonionic surfactant.

6. The mineral-containing composition according to claim 5, wherein said nonionic surfactant is at least one compound selected from the group consisting of glycerol fatty acid esters, polyglycerol fatty acid esters, sucrose fatty acid esters, propylene glycol fatty acid esters and sorbitan fatty acid esters.

7. The mineral-containing composition according to claim 6, wherein said polyglycerol fatty acid esters comprise a polyglycerol moiety having a degree of polymerization of 3 or more in an amount of 70% by weight or more.

8. The mineral-containing composition according to claim 1, wherein the water-insoluble mineral is obtained by a method for forming salts by neutralization in the presence of the enzymatically decomposed lecithin.

9. The mineral-containing composition according to claim 1, wherein 80 vol % or more of the water-insoluble mineral have a particle size of 0.2 µm or less.

10. Food prepared by adding thereto a mineral-containing composition comprising enzymatically decomposed lecithin and a water-insoluble mineral, wherein said water-insoluble mineral comprises fine particles having a particle size of 0.4 µm or less.

11. The food according to claim 9, wherein said mineral-containing composition further comprises a nonionic surfactant.

12. The mineral-containing composition according to claim 10, wherein 80 vol % or more of the water-insoluble mineral have a particle size of 0.2 µm or less.

* * * * *